United States Patent
Burton et al.

(10) Patent No.: US 6,506,482 B1
(45) Date of Patent: Jan. 14, 2003

(54) VITREOUS CARBON COMPOSITE AND METHOD OF MAKING AND USING SAME

(75) Inventors: Ralph A. Burton, Raleigh, NC (US); Ralph G. Burton, Raleigh, NC (US)

(73) Assignee: Carbon Ceramics Company, LLC, Raleigh, NC (US)

(*) Notice: Subject to any disclaimer, the term of this patent is extended or adjusted under 35 U.S.C. 154(b) by 0 days.

(21) Appl. No.: 09/317,285

(22) Filed: May 24, 1999

(51) Int. Cl.[7] .............................................. B32B 17/12
(52) U.S. Cl. ................. 428/293.4; 428/292.1; 428/293.7; 428/368; 428/401
(58) Field of Search ........................... 428/292.1, 293.4, 428/293.7, 368, 401

(56) References Cited

U.S. PATENT DOCUMENTS

| | | | |
|---|---|---|---|
| 3,109,712 A | 11/1963 | Redfern | 23/209.2 |
| 3,284,371 A | 11/1966 | Krellner | 252/502 |
| 3,626,042 A | 12/1971 | Appleby | 264/29 |
| 3,719,452 A | 3/1973 | Accountius | 423/449 |
| 3,790,393 A | 2/1974 | Cowland et al. | 106/56 |
| 4,137,477 A | 1/1979 | Krol et al. | 313/348 |
| 4,143,292 A | 3/1979 | Hosoki et al. | 313/336 |
| 4,188,369 A | 2/1980 | Rautavuori et al. | 423/449 |
| 4,198,382 A | 4/1980 | Matsui | 423/445 |
| 4,225,569 A | 9/1980 | Matsui et al. | 423/445 |
| 4,504,441 A | 3/1985 | Kuyper | 419/35 |
| 4,526,924 A | 7/1985 | Korb et al. | 524/541 |
| 4,634,531 A | 1/1987 | Nakagawa et al. | 210/639 |
| 5,182,166 A | 1/1993 | Burton et al. | 428/368 |

FOREIGN PATENT DOCUMENTS

| | | |
|---|---|---|
| GB | 593477 | 10/1947 |
| GB | 624312 | 6/1949 |
| WO | WO 91/16826 | 11/1991 |

OTHER PUBLICATIONS

Vitreous Carbon matrix for Low–Wear Carbon/Metal Current Collectors, Burton, R.A. et al., IEEE Transactions on Components, Hybrids, and Manu. Technology, vol. 12, No. 2, 1989, pp.224–228.
Tribology of Carbon Matrix Composites, Burton, R.G. et al.
Quacorr 1001 Resin, Material Safety Date Sheet (5 pages) from QO Chemicals Oakbrook, IL Feb. 1985.
Ultra Low Wear in Carbon Matrix Materials, Burton, R.A., et al.
Electrical Contracts and Electromechanical Components, Proceedings of the International Conference on Electrical Contacts. Beijing, China May 9, 1989 pp. 67–77.
Laser Machining for Advanced Seals, Burton, R.A. et al.
Friction and Wear of Glassy Carbon in Sliding Contact, Burton, R.A. et al., Final Report, U.S. Dept. of Energy Contract No. DE–AC02–88 CE 9007, Sep. 1, 1989.

*Primary Examiner*—Edward J. Cain
(74) *Attorney, Agent, or Firm*—Steven J. Hultquist; Marianne Fuierer; Yongzhi Yang

(57) ABSTRACT

A reinforced vitreous carbon composite suitable for use in the formation of wear-resistant assemblies, such as joint prosthetic devices, bearings, current collectors, sealing components, brake linings, electrical motor brushes, and other tribological products. The reinforced composite is formed by impregnating a metal reinforcement structure with a furfuryl alcohol resin, and polymerizing the resin while thermally managing the polymerization process, to produce a poly(furfuryl) alcohol continuous phase that is isotropic, homogeneous and essentially completely void-free, e.g., in a bulk composite form having dimensions greater than 25 millimeters in each of the x, y and z directions thereof.

81 Claims, 3 Drawing Sheets

VITREOUS CARBON COMPOSITE AND METHOD OF MAKING AND USING SAME

CROSS-REFERENCE TO RELATED PATENT

The disclosure of U.S. Pat. No. 5,182,166 issued Jan. 26, 1993 to Ralph A. Burton and Ralph G. Burton for "Wear-Resistant Composite Structure of Vitreous Carbon Containing Convoluted Fibers" is hereby incorporated herein by reference in its entirety.

BACKGROUND OF THE INVENTION

1. Field of the Invention

The present invention relates generally to reinforced vitreous carbon composites and methods of making and using the same.

2. Description of the Related Art

U.S. Pat. No. 5,182,166 issued Jan. 26, 1993 describes a wear-resistant vitreous carbon composite containing convoluted reinforcement fibers, and a method of making and using same.

The composite and methodology of U.S. Pat. No. 5,182,166 resolve cracking issues involved in pyrolyzed glassy carbon composites of the prior art, by the provision of convoluted fibers producing a highly improved crack-resistant character to the composite mateial. Further, from the standpoint of tribological properties, the vitreous carbon composites of U.S. Pat. No. 5,182,166 provide markedly improved wear-resistance, as compared with pyrolyzed glassy carbon composite materials of the prior art.

The invention herein disclosed embodies various improvements in the composites technology disclosed in such U.S. Pat. No. 5,182,166.

In the polymerization of liquid-phase monomeric or oligomeric organic materials to provide a polymer that is pyrolizable to form vitreous carbon as a continuous phase material for a reinforced vitreous composite, the polymerization reaction involves (1)joining of molecules of the monomer and/or oligomer into multi-molecule chains and (2) cross-linking of these chains by chemical bonds. This process is exothermic and the released heat of polymerization is substantially trapped in the polymerizing liquid resin, since the liquid resin is a poor conductor of heat. Such heat of polymerization reaction is sufficient to bring the resin to a temperature above its boiling point, and even cup-full amounts will foam and fume.

In consequence, the composite formed from such a resin will correspondingly contain foaming and fuming defects in the structure of the polymerized material, which then in subsequence pyrolysis will be retained as material defects of the continuous phase material. The product composite then is non-homogeneous and non-isotropic in character, containing gross voids or pores, and cannot be used in applications where uniformity of the morphology and of the structural/performance properties of the composite material are required.

Conversely, when the reaction rate of the polymerization is low, as a result of low temperature and/or low concentrations of polymerization catalyst, the product "green body" material is leathery in texture and does not yield good carbon bodies on subsequent firing for pyrolysis of the polymer.

These problems are resolved by the composite material herein disclosed and the process herein disclosed of making same.

SUMMARY OF THE INVENTION

In one aspect, the present invention relates to a metal-reinforced vitreous carbon composite including a metal fiber discontinuous phase in a continuous phase vitreous carbon that is essentially free of foam and fume indicia, wherein the composite is of a three dimensional character having each of its dimensions being at least 25 millimeters.

Another aspect of the invention relates to a metal-reinforced carbon composite including a metal fiber discontinuous phase in a continuous phase vitreous carbon that has been formed by polymerization of a continuous phase precursor material comprising furfuryl alcohol monomer and/or oligomer, followed by pyrolysis of the polymerized material, wherein the polymerization is carried out under polymerization conditions below the boiling point of the precursor material, and wherein the composite is of a three dimensional character having each of its dimensions being at least 25 millimeters.

A still further aspect of the invention relates to a metal-reinforced vitreous carbon composite including a metal fiber discontinuous phase in a continuous phase pyrolyzed poly (furfuryl alcohol) vitreous carbon material wherein the composite is of a three dimensional character with each of its dimensions being at least 25 millimeters and wherein the composite is substantially completely void-free in character.

A further aspect of the invention relates to a vitreous carbon composite including a continuous phase of pyrolyzed poly(furfuryl alcohol) vitreous carbon material polymerized and pyrolyzed about a discontinuous silicon bronze material to form a composite structure including a carbocupric reaction product as a third phase material between the vitreous carbon continous phase and the discontinuous silicon bronze material.

In another aspect, the invention relates to a metal-reinforced vitreous carbon composite including a metal fiber first discontinuous phase and a thermally non-conductive second discontinuous phase in a continuous phase pyrolyzed poly(furfuryl alcohol) vitreous carbon material.

A further aspect of the invention relates to a metal-reinforced vitreous carbon composite including a needle-punched metal wool discontinuous phase in a continuous phase pyrolyzed poly(furfuryl alcohol) vitreous carbon material.

The invention in other aspects relates to products comprising a metal-reinforced vitreous carbon composite of the invention, such products including third rail current collectors, pantograph assembly, trolley shoes, electrical brushes, seals, bearings, therapeutic structures for implantation in an animal body, e.g., human or other mamallian body, such as a joint replacement structure, etc.

Another aspect of the invention relates to a multilayer laminate material comprising at least one layer of a vitreous carbon composite including a metal fiber discontinuous phase in a continuous phase pyrolyzed poly(furfuryl alcohol) vitreous carbon.

A further aspect of the invention relates to a poly(furfuryl alcohol) film, characterized by a degree of polymerization imparting to the film a flexible character.

A still further aspect of the invention relates to a metal-reinforced poly(furfuryl alcohol) composite green body including a metal fiber discontinuous phase wherein the composite is of a three dimensional character with each of its dimensions being at least 25 millimeters and wherein the composite is substantially completely void-free in character.

In one method aspect, the invention relates to a process for making a metal-reinforced vitreous carbon composite material, comprising the steps of:

providing a mold including therein a mold cavity and wall structure bounding the mold cavity, wherein the wall structure is formed of a thermally conductive material at a wall thickness providing a substantial thermal heat sink for heat of polymerization of a material polymerized in the mold cavity;

disposing in said mold cavity a metal fiber matrix defining a three-dimensional structure including void space therein;

compressing the three-dimensional structure in the mold, e.g., to laterally conform the structure to the wall structure of the mold cavity while retaining void space therein;

partially polymerizing exterior to the mold cavity a continuous phase precursor material comprising (i) a poly (furfuryl alcohol) monomer and/or oligomer and (ii) a polymerization catalyst, to conduct an exothermic polymerization reaction generating a heat of polymerization;

removing from the partially polymerized precursor material at least part of the heat of polymerization therefrom exterior of the mold cavity;

introducing the partially polymerized precursor material, subsequent to removal of at least part of the heat of polymerization therefrom, into the mold cavity; compressively consolidating the partially polymerized precursor material with the three-dimensional structure in the mold cavity under polymerization conditions to form a metal-reinforced polymer composite material; and subjecting the metal-reinforced polymer composite material to pyrolysis conditions effective to pyrolyze the polymer in the composite material, to yield the metal-reinforced vitreous carbon composite material.

Another aspect of the invention relates to a process for forming a metal-reinforced vitreous carbon composite comprising:

providing a metal fiber discontinuous phase;

impregnating the metal fiber discontinuous phase with a precursor including (i) furfuryl alcohol monomer and/or oligomer and (ii) a polymerization catalyst;

polymerizing the precursor;

removing exothermic heat of polymerization from the precursor to maintain temperature of the precursor in a temperature range of from about 40° C. to about 100° C., and gel time of the precursor in a range of from about 2 to 30 minutes; and pyrolyzing polymerized precursor to yield the metal-reinforced vitreous carbon composite.

Other aspects and features will be more fully apparent from the ensuing disclosure and appended claims.

DETAILED DESCRIPTION OF THE INVENTION, AND PREFERRED EMBODIMENTS THEREOF

Figure 1:
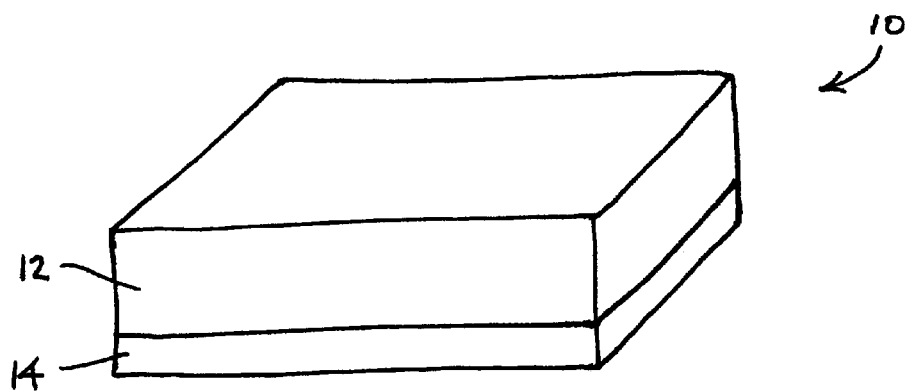
FIG. 1 is a perspective view of a vitreous carbon composite structure in accordance with one embodiment of the present invention.

The present invention is based, inter alia, on the discovery that vitreous composites of a highly superior character can be formed by use of appropriate thermal management techniques in the polymerization process by which the liquid resin for the continuous phase material is converted to a polymer that in turn may be pyrolyzed to yield the vitreous carbon continous phase of the composite.

The liquid resin may comprise monomer and/or oligomer for the continuous phase material, and the processing of the resin to form the polymer involves a balance of the degree of polymerization of the resin, the rate of heat removal from the resin, and the process conditions of the polymerization, so that the polymerization process is managed to produce a polymer composite that will be essentially free of voids, foaming and fume tracks, and other morphological abnormalities. In this manner, a composite can be produced that is homogeneous, isotropic and possessed of good structural and performance, e.g., wear-resistance, properties.

The resin used in the practice of the present invention preferably comprises a furfuryl alcohol monomer and/or oligomer, although any suitable materials described in the aforementioned U.S. Pat. No. 5,182,166 may be usefully employed. A particularly preferred furfuryl alcohol resin is the resin commercially available from QO Chemicals, Inc. under the trademark QUACORR, utilized with a polymerization catalyst, such as a thermally activated polymerization catalyst. Various Lewis acid catalysts can be utilized, as well as any other suitable catalytically effective materials. A particularly preferred polymerization catalyst comprises maleic acid or maleic anhydride.

Preferably, the polymerization process involving the resin is carried out with thermal management of the process so that the discontinous phase reinforcement medium of the composite precursor serves to conduct heat of polymerization out of the resin, and the polymerization is carried out in a vessel having sufficient thermal ballast (heat capacity) or otherwise provided with cooling capability, so that polymerization is slowly and uniformly carried out, without the runaway polymerization conditions that results in voids, fissures, channel artifacts, and other morphological defects.

In this respect, it may be advantageous to conduct a partial polymerization of the resin prior to impregnation of the resin into the discontinuous phase reinforcement structure, and thereafter conducting the remaining extent of polymerization to form the reinforced polymer composite for subsequent pyrolyzation.

In this respect, the physical properties of the resin will change depending on the extent of its polymerization. The resin if composed solely of a furfuryl alcohol monomer will have a low water-like viscosity, rendering it more easily impregnated into the discontinuous phase reinforcement structure but requiring greater thermal control in the polymerization process since a full extent of heat-releasing exothermic polymerization is required, whereas a resin formed of a highly oligomerized material will be correspondingly more viscous and harder to pump through the process system, and to impregnate in the discontinuous phase reinforcement structure, but countervailingly easier to thermally manage, since less heat-releasing polymerization of the resin will be necessary.

Thermal management may therefore be effected by ex situ polymerization of the resin, prior to introducing same to the polymerization vessel containing the discontinuous phase reinforcement structure. For example, the resin may be utilized as a monomer, or a low molecular weight oligomer, and polymerized in small diameter tubes in a heat exchange, to provide highly effective removal of the exothermic heat energy from the resin prior to its introduction to the polymerization vessel containing the discontinuous phase reinforcement structure.

Further, the thermal management of the polymerization process may involve significant heat transfer and thermal equilibration by virtue of the thermal conductivity of the discontinuous phase reinforcement medium in the composite in which the continuous phase resin is being polymerized. Where the reinforcement phase is formed of a metal, metal alloy or other highly thermally conductive material, the heat of polymerization may be readily channeled out of the bulk interior mass of the resin material through the conductive reinforcement element(s) to the wall surface of the polymerization vessel (mold) in which the heat of polymerization is being generated. Where the wall of the polymerization vessel is of a significant thickness, so as to function as a thermal ballast structural member, the overall heat management in the process system is greatly facilitated.

Alternatively, the resin may be reacted ex situ (outside the polymerization vessel containing the discontinuous phase reinforcement structure) and then quenched to chill the resin to suitably low material to avoid the occurrence of runaway exotherm when the resin is introduced to the vessel containing the discontinuous phase reinforcement structure.

The discontinuous phase reinforcement structure may comprise any suitable medium, preferably of a fibrous character, that will in the subsequent composite provide a uniform reinforcement of the material for the desired morphological characteristics, structural integrity and performance properties for the composite in subsequent use. A preferred type of discontinuous phase reinforcement structure comprises a metal wool of a suitable composition, e.g., a copper, copper alloy, or other metal composition. One particularly preferred metal composition comprises a silicon bronze wool. Other conformations of discontinuous phase reinforcement structure may be employed, such as a knitted fabric structure, scrim, needle punched fabrics, loose fibers, particles, ceramic whiskers, etc.

Metal wools are preferred forms of discontinuous phase reinforcement structures in the broad practice of the present invention, since they may initially be easily cut and shaped to the product composite ultimately desired, and since they are readily compactible in connection subsequent to resin impregnation thereof, to fully fill all interstices of the discontinuous phase reinforcement structure with the resin.

The reinforced composite of the invention may therefore comprise a metal-reinforced vitreous carbon composite including a metal fiber discontinuous phase in a continuous phase vitreous carbon that is essentially free of foam and fume indicia, such as otherwise would result from exotherm of an uncontrolled character, e.g., above the boiling point of the resin. The resulting composite is of a three dimensional bulk character, i.e., having each of its dimensions in the x-, y- and z-axis directions being at least 25 millimeters, preferably more than 75 millimeters, and most preferably more than 100 millimeters. In this respect, it is pointed out that the art heretofore has been unable to make infused metal-carbon composites of homogeneous character and good quality, above 18 millimeters in thickness.

By contrast, the present invention readily permits the fabrication of a metal-reinforced vitreous carbon composite including a metal fiber discontinuous phase in a continuous phase pyrolyzed poly(furfuryl alcohol) vitreous carbon material wherein the composite is substantially completely void-free in character (having less than 5% by volume voids and wherein the average void diameter of such voids is less than 1 $\mu$m).

In the preferred composite of the present invention, the continuous phase vitreous carbon is a polymerization product of furfuryl alcohol, i.e., the continuous phase material is poly(furfuryl alcohol).

In the metal-reinforced composites of the invention, the metal fiber discontinuous phase typically constitutes from about 5% to about 40% by volume of the composite, but may have a greater or lesser volumetric composition in the broad practice of the invention. The metal fiber discontinuous phase in such composites may for example be formed by convoluted fibers having a radius of curvature to fiber diameter ratio of from about 5:1 to about 20:1, wherein both radius of curvature and fiber diameter are in the same units. In preferred metal-reinforced composites of the invention, the metal fiber discontinuous phase content of the material is from about 5% to about 90% by weight. As mentioned, the preferred form of the metal reinforcement is a metal wool, most preferably a silicon bronze wool, although other metals, e.g., copper and copper alloys, noble metals, etc., may be employed to advantage in specific embodiments of the invention. The metal wool may comprise fibers having a mean diameter between about 10 and 100 micrometers and a length of up to several meters, e.g., 3–5 meters or even more, depending on the form of the fibrous metal wool material.

Preferably, the metal fiber discontinuous phase is interspersed throughout the continuous phase of vitreous carbon material in a randomly oriented mesh, although oriented or drawn fiber arrays may be advantageously used within the broad scope of the invention.

A vitreous carbon composite may be formed in one specific embodiment of the invention, including a continuous phase of pyrolyzed poly(furfuryl alcohol) vitreous carbon material polymerized and pyrolyzed about a discontinuous silicon bronze material to form a composite structure including a carbocupric reaction product as a third phase material between the vitreous carbon continous phase and the discontinuous silicon bronze material.

In another particular embodiment, the present invention contemplates a metal-reinforced vitreous carbon composite including a metal fiber first discontinuous phase and a thermally non-conductive second discontinuous phase in a continuous phase pyrolyzed poly(furfuryl alcohol) vitreous carbon material. The metal fiber first discontinous phase may be a metal wool or other form of reinforcing material. The thermally non-conductive second discontinuous phase is utilized as a thermal modulator in the polymerization of the resin, to thermally homogenize the mass of the resin impregnating the reinforcement media, so that excessive heat generation, localized hot spots and other polymerization-associated thermal anomalies may be avoided.

The thermally non-conductive second discontinuous phase may for example comprise particulates of at least one material selected from the group consisting of quartz, silicon, alumina, and silica. A preferred form of the particulates is spheres, such as cenospheres of quartz or other non-metal material.

Regardless of the specific form of the reinforcing phase in the composite, such phase is provided and formed in a manner to accommodate the heat burden of the polymerization operation without undue localization of heat in the polymerizing mass of the resin. A metal wool may be uniformly distributed throughout the volume of the resin, so that the metal serves conductively to equilize the heat that is generated in the polymerization, and to channel it to the margins or periphery of the composite mass being formed.

The reinforcement media will be formed in a manner accommodating the concurrent requirement of impregnating same with the resin so that no voids or unfilled (with the resin) spaces are left in the composite precursor structure. For example, the metal-reinforced vitreous carbon composite may include a needle-punched metal wool discontinuous phase in a continuous phase pyrolyzed poly(furfuryl alcohol) vitreous carbon material.

The reinforced composite material of the invention may be employed in a wide variety of products, including, but not limited to, the following: rail pantograph bars; third rail currrent collectors; inserts for trolley shoes; railroad brakes; apex seals for rotary engine rotors; sleeve bearings; segmented pad bearings; cassettes for bearings to allow conventional tools to be used; instntnent bearings; propeller shaft seals, bearings and assemblies; electrical brushes for large electric motors; piston rings; cylinder walls; valve guides, etc. The composite material of the invention is particularly usefully employed in applications where an inert, highly wear-resistant material is required. The composite material of the invention has a low friction character, and may be processed to remove the surface region metal content so that the surface is formed of the vitreous carbon material only, with a very low friction character.

In this respect, the composite as formed may be subjected to treatment for removal of the metal from a surface layer of the composite, to form a layer of thickness that may extend to any suitable depth from the outer surface, in which the metal content has been removed. Such thickness may for example be on the order of micron or millimeter thicknesses, or greater or lesser thickness, in which the metal has been removed by electrolytic removal methods, chemical etch or solubilization methods, volatilization of the metal, chemical reaction and dissolution processing, etc. Further, the surface after such demetallization may be impregnated in the resulting pores from the demetallization process, with a suitable material such as a lubricant, medicament, etc., to enhance the properties of the surface and the composite in subsequent use. With respect to lubricants, suitable lubricative species include, without limitation, molybdenum sulfide, zinc sulfide, and metal-free phthalocyanin.

As an alternative to surface modification, the composite material of the invention may be formed with a bulk modified character, e.g., where in lieu of a suface impregnated lubricant material, the composite itself may be formed with a suitable lubricant thereof, or with other additive or component in the precursor mixture including the resin and the catalyst. Such bulk additives must of course be appropriately selected so that they are compatible with the processing conditions involved in the polymerization and pyrolysis steps that are employed to form the composite.

In like manner, the surface of the composite material of the invention may be processed, machined, textured, patterned, coated, or otherwise modified so that the composite is rendered suitable for its intended purpose.

The composite material of the invention may also be utilized in forming multilayer laminate structures including at least one layer of a composite material according to the present invention.

The invention also contemplates as an aspect thereof various intermediates in the preparation of the composite of the invention. As one example of such an intermediate, the invention comprehends a metal-reinforced poly(furfuryl alcohol) composite green body including a metal fiber discontinuous phase in which the composite is substantially completely void-free in character, with each of its x-, y- and z-axis dimensions being at least 25 millimeters.

The invention relates in another aspect to a poly(furfuryl alcohol) film, characterized by a degree of polymerization imparting to the film a flexible character. It has been discovered that the preferred furfuryl alcohol monomer and/or oligomer can be partially polymerized to form a flexible film material when cast at low thicknesses. The film may for example have a thickness in the range of from about 0.1 to about 2,000 $\mu$m.

The carbon composite material of the present invention may be formed in any suitable manner, e.g., in a manner as generally described in the aforementioned U.S. Pat. No. 5,182,166, as modified in accordance with the disclosure herein.

The process of making a metal-reinforced vitreous carbon composite material in accordance with the process of the present invention, may suitably comprise the provision of a mold including a wall structure bounding a mold cavity. The wall structure is preferably formed of a thermally conductive material at a wall thickness providing a substantial thermal heat sink for heat of polymerization of a material polymerized in the mold cavity. Suitable materials for such purpose include metals, ceramics, etc. that are stable at the temperatures and under the process conditions employed.

A metal fiber matrix defining a three-dimensional structure including void space therein, e.g., a metal wool body, is disposed in the mold cavity, and such three-dimensional structure is compressed in the mold, e.g., to laterally conform the structure to the wall structure of the mold cavity, while retaining void space in the three-dimensional structure. A continuous phase precursor material comprising (i) a poly(furfuryl alcohol) monomer and/or oligomer and (ii) a polymerization catalyst, is partially polymerized exterior to the mold cavity, to carry out an exothermic polymerization reaction generating a heat of polymerization. At least part of this heat of polymerization is removed from the partially polymerized precursor material exterior of the mold cavity. The partially polymerized precursor material, subsequent to removal of at least part of the heat of polymerization therefrom, is introduced into the mold cavity, and compressively consolidated with the three-dimensional structure in the mold cavity under polymerization conditions to form a metal-reinforced polymer composite material. Subsequent to such polymerization, the metal-reinforced polymer composite material is subjected to pyrolysis conditions effective to pyrolize the polymer in the composite material, to thereby yield the metal-reinforced vitreous carbon composite material.

To remove at least part of the heat of polymerization from the partially polymerized precursor material exterior of the mold cavity, the precursor material may be flowed to the mold cavity along a flow path in which the precursor material is heated to promote its partial polymerization and subsequently is quenched to remove the heat of polymerization therefrom.

As another variation, the polymerization reaction may be selectively quenched by neutralizing the catalyst to provide a predetermined degree of polymerization, at the desired stage(s) of the process. As another thermal management technique, the flow path by which the monomer and/or oligomer precursor is flowed into the polymerization chamber containing the reinforcement medium, may be branched into multiple paths in proximity to the mold, whereby quenching of the heat of polymerization is improved over a single path flow of precursor material into the mold (i.e., by using smaller diameter flow passages that are more easily jacketed, or equipped with extended area fins for heat transfer at a higher surface area to volume of precursor level, etc.).

A moveable wall member may be disposed in the mold cavity to subject the three dimensional structure to compression in step (c) and to compressively consolidate the partially polymerized precursor material with the three-dimensional structure in the mold cavity under polymerization conditions. The polymerization conditions may usefully include heat transfer between the precursor material and the wall structure of the mold.

The metal-reinforced polymer composite material produced by the above-described process may be subjected to ancillary treatment, e.g., shaping, machining, etc., prior to subjecting the material to pyrolysis. For example, the process may include the step of lasing a surface of the metal-reinforced vitreous carbon composite material, or alternatively etching such surface, to form a textured surface thereon. The process may as a still further alternative comprise the step of in-casting a gauze at a surface of the metal-reinforced vitreous carbon composite material to form such a textured surface thereon. As discussed hereinabove, the surface of the composite material may be treated, such as by electrolytically demetallizing the metal-reinforced vitreous carbon composite material at a surface thereof. The electrolytic demetallization may be effected by jet impingement of an aqueous electrolytic medium on the surface of the metal-reinforced vitreous carbon composite material.

In one particular embodiment of the invention relating to the formation of a laminate comprising a metal-reinforced vitreous carbon composite material of the invention, a metal bar may be inserted into the metal-reinforced polymeric composite material prior to pyrolysis, so that the pyrolysis conditions yield a laminated structural assembly.

In general, the pyrolysis step to which the polymeric composite is subjected to form the vitreous carbon composite of the invention, the pyrolysis conditions may comprise any suitable process conditions and treatment steps yielding a vitreous carbon composite of the desired character. For example, the pyrolysis conditions may comprise low frequency induction heating of the metal-reinforced polymeric composite material, ultrasonic heating of the metal-reinforced polymeric composite material, conductive heating of the metal-reinforced polymeric composite material, convective heating of the metal-reinforced polymeric composite material, microwave heating of the metal-reinforced polymeric composite material, infrared heating of the metal-reinforced polymeric composite material, or any other suitable manner providing the time and temperature processing necessary for pyrolysis of the polymer in the composite. Illustrative pyrolysis conditions are set out in the aforementioned U.S. Pat. No. 5,182,166.

After its formation, the reinforced vitreous carbon composite material may be utilized in any suitable form, and it may for example be bonded to another structural member to form a laminated composite article, e.g., a seal assembly, a bearing assembly, a rotary engine rotor tip assembly; a piston ring; an implantable therapeutic structural assembly such as a joint prosthesis; a pantograph bar assembly; a third rail current collector assembly; a trolley shoe assembly; an electrical brush assembly; etc.

In a preferred embodiment of the inventive process for forming a metal-reinforced vitreous carbon composite, a metal fiber discontinuous phase is impregnated with a precursor including (i) furfuryl alcohol monomer and/or oligomer and (ii) a polymerization catalyst. The precursor then is polymerized, while removing exothermic heat of polymerization from the precursor to maintain temperature of the precursor in a temperature range of from about 40° C. to about 100° C., and gel time of the precursor in a range of from about 2 to 30 minutes, more preferably in a range of from about 3 to about 20 minutes, and most preferably in a range of from about 4 to about 18 minutes. After the polymerization has been completed, the polymerized precursor is pyrolyzed to yield the metal-reinforced vitreous carbon composite. As used in such context, the term "gel time" refers to the length of time required for a volume of the precursor containing the resin and the polymerization catalyst to reach a solid, non-flowable state, i.e., to "gel."

Referring now to the drawings, FIG. 1 is a perspective view of a composite structure 10 in accordance with one embodiment of the present invention, including a base member 14 having a main body of reinforced vitreous carbon 12 thereon formed in accordance with the present invention.

The composite structure of FIG. 1 may for example form a portion of an electrical motor brush or a brake lining or a prosthetic joint implant or any other of the product structures illustratively discussed herein or otherwise susceptible of fabrication in accordance with the present invention.

In one embodiment, the reinforcement in the reinforced composite structure of FIG. 1 may comprise convoluted fibers having a wool or mesh conformation and uniformly dispersed throughout the vitreous carbon so that these fibers touch only at occasional points. The precise fiber content of the overall composite may vary depending upon its intended use and depending upon the particular fibers selected as well as the resulting properties of the composite material.

Generally speaking, however, the fiber content may vary from about 5% to about 40% by volume, or even more, preferably between 10% and 25% by volume, and from about 5% to about 90% by weight, and preferably between 30% and 80% by weight, for fibrous reinforcement materials such as copper-based mesh. Because the mesh or wool fibers are spatially nearly constant throughout the vitreous carbon, the void space of the fiber matrix (before impregnation with resin or other vitreous carbon precursor material) may for example vary from about 60% to about 95%, and preferably from 75% to 90% (which are the complement of the volume percent ranges).

The preferred fibers are silicon bronze wool fibers displaying irregular cross sections and a mean diameter between about 30 and 100 microns, most preferably between about 30 and 50 microns. These fibers may be cut as short as 1 cm and may in individual lengths be up to approximately 1 meter long or even longer. The fibers usefully employed in the composites of the invention may suitably be made by known cutting or turning processes which guarantee that they are inherently wavy or convoluted. The fibers can be rolled from a spool and be of sufficient length relative to the spool so as to have made several revolutions around the spool. The convolution of the fibers can be achieved by providing a wool or mesh (or woven) configuration, or alternatively a population or array of oriented fibers may be employed.

The present invention is not limited to wool forms or specific metal fibers. Fibers of materials such as nickel, cotton, and paper, as well as other suitable materials, are also compatible with the present invention, although metal fibers are preferred, most preferably copper, copper alloy (brass or bronze, and particularly silicon bronze), nickel, nickel alloy, Hastelloy, titanium and chrome-plated steel.

Still referring to FIG. 1, the composite structure 10 is shown in the form of a block of reinforced vitreous carbon material 12 supported on a base 14. In this regard, it is to be understood that the composite structure is depicted diagrammatically and for illustrative purposes only. The composite structure can be readily formed into the shape shown as well as into other desired shapes for the desired end use to which the composite structure is to be applied.

The reinforced vitreous carbon product may for example be ground, electric discharge machined, ultrasonically machined, lapped, abraded (e.g., with an abrasive solid medium, or alternatively with a fluid medium, such as a water jet), polished, rubbed, diamond sawn and diamond drilled. The polished or lapped surface of the material may be engraved by laser machining. Further, ground balls from the vitreous carbon composite material have been provided, and it has been demonstrated experimentally that they will sustain sufficient stress to be useful in self-lubricated ball bearings.

Moreover, embedded objects of metal or ceramic may be carried through the firing sequence without damage to the ultimate product. Particularly successfully has been the embedding of copper or copper alloy tubes, which may serve as electrical connectors, or threadable anchors for screws. Embedded bodies may also serve as connectors for soldering. In addition, it has been demonstrated that solder will wet and bond to the exposed fiber-metal in the face of the cut, lapped, or polished composite.

As indicated above, a preferred fiber reinforcement material is a mesh or wool of copper alloy fibers. These preferred fibers may suitably have a diameter of 30–50 microns, with a composition (in weight percent) of, e.g., 0.05% lead, 0.10% iron, 0.15% tin, 0.20% zinc, 0.10% aluminum, 1.1% silicon, 0.1% nickel, and the balance copper. The lower limit for the length of the fibers is on the order of about 1 cm. Preferred convoluted fibers have a radius of curvature/diameter ratio which is in the range of about 5:1 to about 20:1 (the radius of curvature and the diameter being measured in the same dimensional units).

Still referring specifically to the preferred copper or copper-based fibers, it should be noted that the elastic modulus of copper is five times greater than the elastic modulus of vitreous carbon and, hence, is therefore five times stiffer. However, the yield strength is about the same for both, and hence, the matrix material has greater permissible elongation before yield. Therefore, where coupled at an interface, the copper would yield first, absorbing considerable energy. This effect is believed to substantially toughen the end product.

Figure 2:
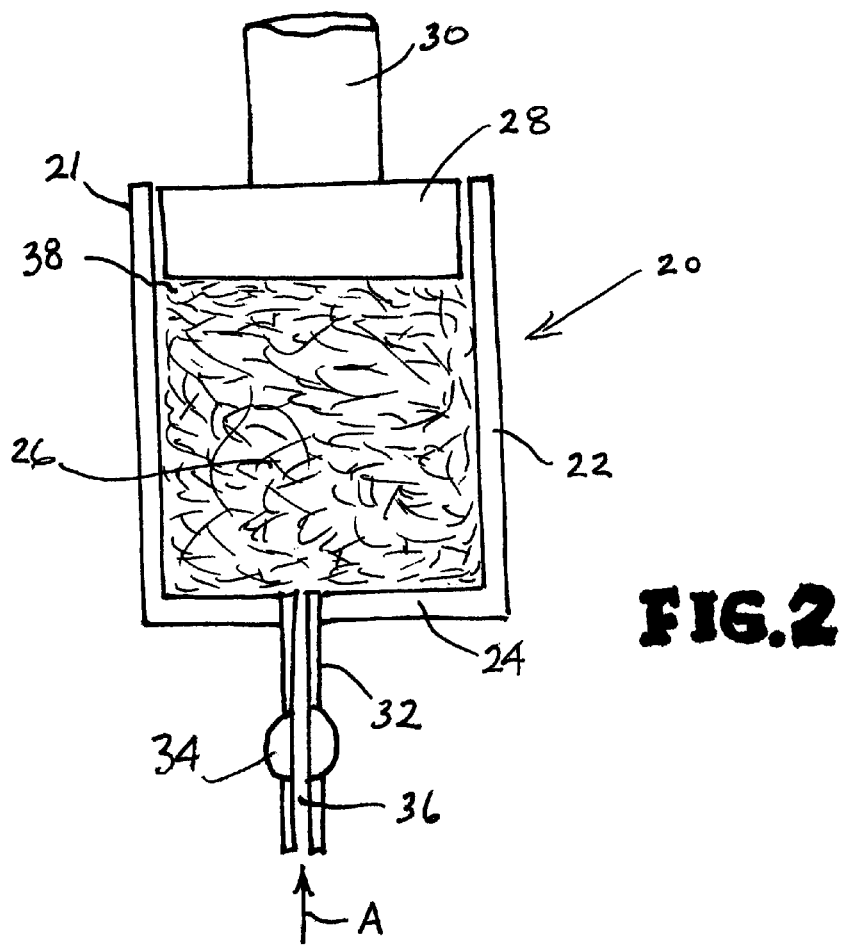
FIG. 2 is a front elevational view, in partial cross-section, of a polymerization system in accordance with one embodiment of the present invention, showing a reinforcement phase material positioned in the polymerization vessel.

Referring now to FIG. 2, there is shown a front elevational view, in partial cross-section, of a polymerization system 20 in accordance with one embodiment of the present invention, showing a reinforcement phase material 26 positioned in the interior volume 38 of a polymerization vessel 21. The polymerization vessel 21 includes a floor 24 and side wall 22 bounding the interior volume 38.

As shown, the reinforcement phase material 26 is deployed in the form of a bat of wool, on the upper face of which is positioned a piston 28, joined in turn to reciprocatable shaft 30 coupled with suitable drive means (not shown) such as an electric or combustion drive motor, power take-off, transmission, or other motive driver which is selectively actuatable to cause the downward or upward movement of the shaft and associated piston, at the rate and in the direction desired.

At the floor of the vessel 21 is a resin feed tube 32 defining an interior passage 36 communicating with the interior volume 38 of the vessel, with the resin feed tube having a flow control valve 34 therein. The valve 34 is selectively actuatable to open or close same as desired, and the resin feed tube is coupled to a source of resin (not shown).

The mass of reinforcement phase material 26 in the vessel 21 may be slightly compressed after introduction of such material into the interior volume of the vessel, by downwardly translating the piston 28 against the material, to cause it to conform to the shape of the containing vessel.

Next, the resin is injected into the interior volume 38 from the interior passage 36 of the resin feed tube, with valve 34 open, as shown. The resin is introduced under sufficient pressure to cause it to penetrate and ingress to the interior spaces of the mat of reinforcement phase material 26, so that the mat of reinforcement phase material 26 is saturated with the resin. Next, the piston is further downwardly translated to the piston position shown in FIG. 3.

Figure 3:
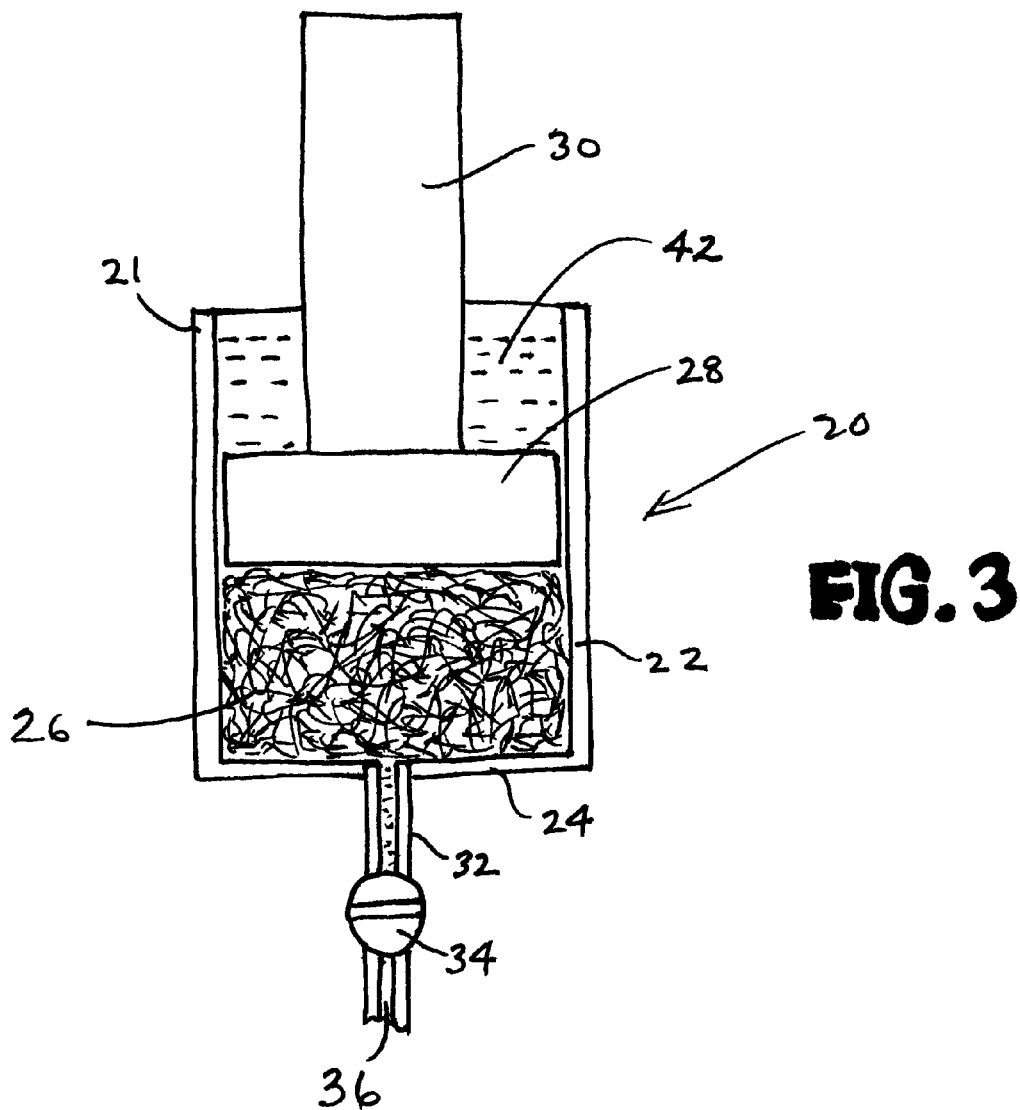
FIG. 3 is a front elevation view of the polymerization system of FIG. 2, after compression of the reinforcement phase material and inpregnation thereof with resin.

FIG. 3 is a front elevation view of the polymerization system of FIG. 2, after compression of the reinforcement phase material and impregnation thereof with resin 42. As shown in FIG. 3, the valve 34 in the resin feed tube 32 is closed, and the downward translation of the piston 38 has forced excess resin material to be displaced from the mat of reinforcement phase material 26, to above the piston (from which the resin can be withdrawn from the vessel, to allow subsequent retraction of the piston from the vessel after the polymerization of the resin has taken place).

While the resin-saturated mat is under pressure, the resin is undergoing polymerization by reason of the polymerization catalyst mixed into the precursor mixture. Heat of polymerization may be dissipated from the resin in the vessel, through the walls and floor of the vessel. The walls and floor of the vessel may be of an appropriate thickness to constitute a thermal ballast in this respect, to maintain the temperature of the resin at a desired level or range. Further, the vessel may be jacketed, or otherwise provided with appropriate thermal control means, such as heat transfer surface, heat exchange passages in the wall accommodating flow of a coolant/heating medium therethrough. Any suitable means of thermal management may be employed for this purpose.

In addition, the resin may as previously described, be subjected to ex situ polymerization outside of the polymerization vessel 21, to partially pre-react the resin and dissipate the heat of polymerization therefrom. A flow system may be employed by which the resin is warmed in the admission galleries to the polymerization vessel (mold). This reduces the viscosity of the resin, making it easier to flow to the polymerization vessel through the associated piping and feed structure (pumps, flow meters, etc.).

In the FIG. 3 system, the resin is pumped into the fiber body through the resin feed line, and residual air in the interior volume cavity escapes around the loosely fitted piston. When surplus fluid begins to appear around the piston, the resin feed valve is closed, and the piston is forced further down, compacting the fiber body, and squeezing out the excess resin therefrom.

The two-step compaction process just described serves to ensure good homogeneity of distribution of the reinforcement phase material 26 in the interior volume of the vessel 21. Localized variation of the compaction density can be further minimized when the bed of fiber is "needle punched" or "picked." This process involves passing hooked needles into the mat of compacted fiber and then withdrawing them, to pull fiber clusters across the boundaries of the intact layers in the bed. This process is used to prepare filter media and can be applied to beds of fibers in the practice of the present invention, e.g., before the mat of fibers is dropped into the vessel 21, and optionally after the mat has been filled with resin, to further densify the mat.

Accordingly, the process in the FIGS. 2 and 3 system may comprise preparing the fiber body (mat or wool of fibers) at a reduced density, followed by placement of the fiber body into the vessel cavity, pre-pressing the fiber body to ensure conformance with the vessel interior cavity, injecting resin and post-pressing the fiber body to consolidate and densify the bed of fiber, with subsequent polymerization to form the reinforced polymer body. The resin can be cured by several means, depending on the material chosen: the action of a catalyst or a hardener, the cooling of the resin, and/or thermal activation of the polymerization reaction, through a latent catalyst, using a temperature controlled vessel as the mold for the composite body.

The resulting polymerized composite body can then be removed from the vessel and placed in a furnace or other pyrolyzation apparatus and subjected to pyrolysis conditions effective to convert the reinforced polymer composite to a vitreous carbon composite.

The resin as originally introduced to the vessel cavity may be mixed with a component such as cenospheres, which lightens the composite body, reduces polymer cost and consumption, and moderates the heat release in the polymerization step per unit volume, thereby providing reduced production costs for the reinforced composite, relative to a corresponding reinforced composite not containing such added thermal moderation component.

In presently preferred practice of the present invention, the resin comprises a furfuryl alcohol monomer that is partially polymerized outside the polymerization vessel with an acid catalyst, with the reaction being quenched by neutralizing the catalyst. Before injection of the oligomer into the polymerization vessel, fresh catalyst is added and a typical gel time of about 10 minutes is achieved.

Figure 4:
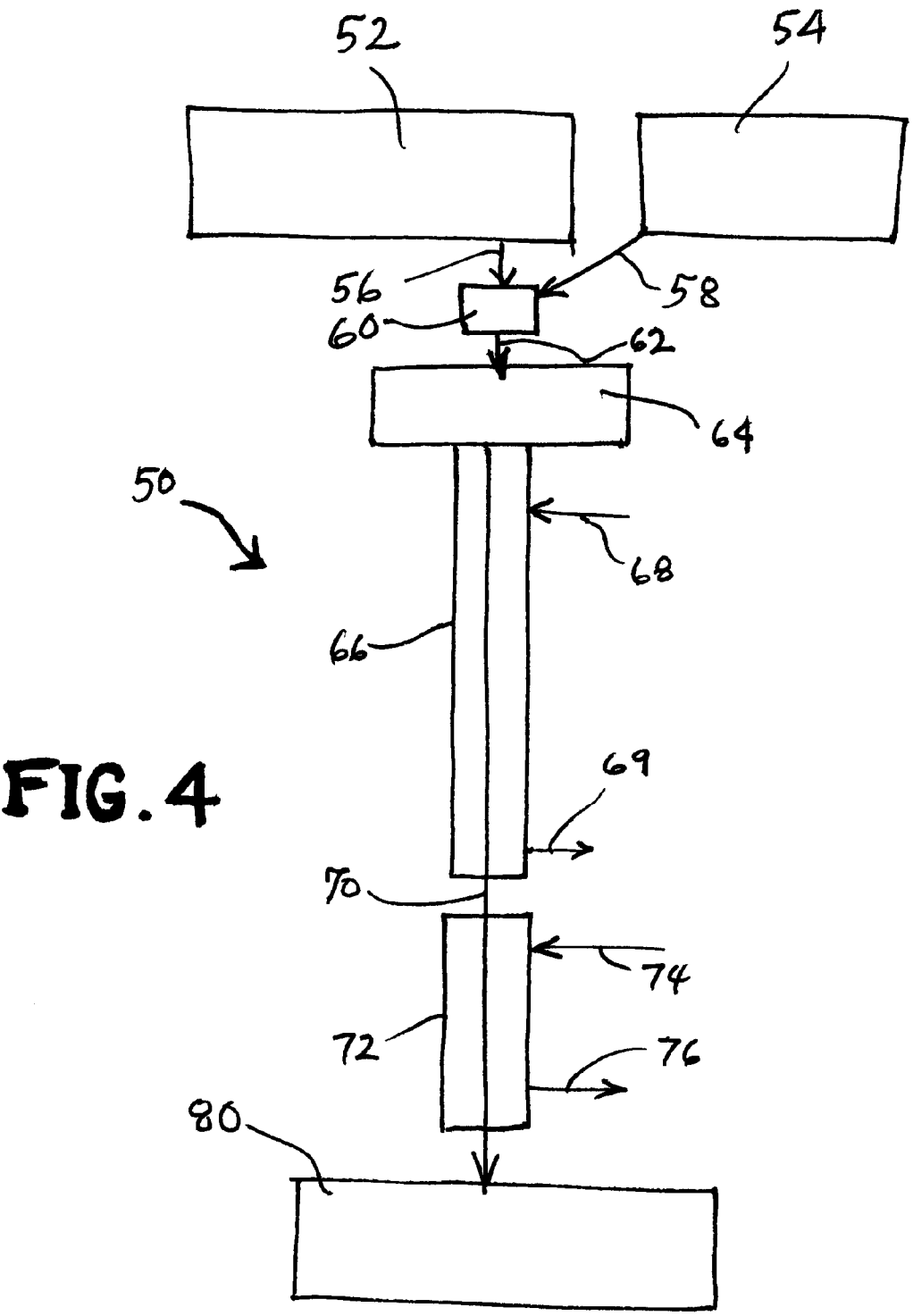
FIG. 4 is a simplified schematic view of a polymerization system according to a further embodiment of the present invention.

FIG. 4 is a simplified schematic view of a polymerization system 50 according to a further embodiment of the present invention. For thermal control of pre-polymerization of the resin material, a monomer from monomer source vessel 52 is introduced by line 56 to a mixer 60 concurrently with polymerization catalyst flowed from catalyst supply vessel 54 in line 58 to the mixer 60. The resulting precursor mixture then passes by line 62 to pump 64. The pump 64 causes the flow of the precursor mixture down the small diameter line 70 through jacketed tube 66 equipped with a warm water inlet 68 and a warm water outlet 69.

Thus, the reacting fluid flows down the tube 70 with wall temperature controlled by a forced external heat transfer medium (warm water). The fluid then moves to a section of tubing 72 with reduced temperature sufficient to quench the reaction, or to slow it to a local gel time of several minutes. This involves forced flow of cooling water through the jacket of tube 72, equipped with water inlet 74 and water outlet 76.

The precursor fluid then flows in line 70 into the mold 80, the bed of fiber therein is compacted by pressing same, and the polymerization process is completed by application of heat to the mold. The preferred temperature for the polymerization of the resin in the mold is in the range of from about 0 to about 100° C.

Thus, in the FIG. 4 system, substantial reaction of the resin takes place in the warmed tube 66, then the resin is substantially quenched in the cold tube 72 before being passed to the loosely packed fiber bed in the mold.

The interior surfaces of the mold may have a mold release agent applied thereto, to facilitate the release of the polymerized composite body from the mold after the desired extent of polymerization has taken place.

The removed polymerized composite body then is pyrolyzed to vitrify the polymer and form the reinforced vitreous carbon composite.

While the invention has been described herein with reference to illustrative features, aspects and embodiments, it will be realized that the scope and utility of the invention are not thus limited, but rather extend to and encompass other variations, modifications and other embodiments, as will readily suggest themselves to those of ordinary skill in the art, based on the disclosure herein. The invention therefore is intended to be construed as including all such variations, modifications and other embodiments, within the spirit and scope of the invention as claimed.

What is claimed is:

1. A metal-reinforced vitreous carbon composite including a metal fiber discontinuous phase in a continuous phase vitreous carbon that is essentially free of foam and fume indicia, wherein the composite is of a three dimensional character having each of its dimensions being at least 25 millimeters.

2. A metal-reinforced carbon composite including a metal fiber discontinuous phase in a continuous phase vitreous carbon that has been formed by polymerization of a continuous phase precursor material comprising furfuryl alcohol monomer and/or oligomer, wherein said polymerization is carried out under thermally managed polymerization conditions below the boiling point of the precursor material, and wherein the composite is of a three dimensional character having each of its dimensions being at least 25 millimeters.

3. A metal-reinforced vitreous carbon composite including a metal fiber discontinuous phase in a continuous phase vitreous carbon that has been formed by polymerization of a continuous phase precursor material comprising furfuryl alcohol monomer and/or oligomer, followed by pyrolysis of the polymerized material, wherein said polymerization is carried out under thermally managed polymerization conditions below the boiling point of the precursor material, and wherein the composite is of a three dimensional character having each of its dimensions being at least 25 millimeters.

4. A metal-reinforced vitreous carbon composite including a metal fiber discontinuous phase in a continuous phase pyrolyzed poly(furfuryl alcohol) vitreous carbon material wherein the composite is of a three dimensional character with each of its dimensions being at least 25 millimeters and wherein the composite is essentially free of foam and fume indicia.

5. The composite of claim 1, wherein the continuous phase vitreous carbon is a polymerization product of furfuryl alcohol.

6. The composite of claim 1, wherein the metal fiber discontinuous phase constitutes from about 5% to about 40% by volume of the composite.

7. The composite of claim 1, wherein the metal fiber discontinuous phase is formed by convoluted fibers radius of curvature to fiber diameter ratio of from about 5:1 to about 20:1, wherein both radius of curvature and fiber diameter are in the same units of measurement.

8. The composite of claim 1, wherein the metal fiber discontinuous phase content of the material is from about 5% to about 90% by weight.

9. The composite of claim 1, wherein said metal fiber discontinuous phase comprises a metal wool.

10. The composite material of claim 9, wherein said metal wool comprises fibers having a mean diameter between about 10 and 100 micrometers and a length of up to about several meters.

11. The composite of claim 1, wherein said vitreous carbon material is formed from a liquid precursor material that has been polymerized by means of a catalyst and then pyrolyzed.

12. The composite of claim 1, wherein said metal fiber discontinuous phase is interspersed throughout said continuous phase of vitreous carbon material in a randomly oriented mesh.

13. The composite of claim 1, wherein each of said dimensions is at least 75 millimeters.

14. The composite of claim 1, wherein each of said dimensions is at least 100 millimeters.

15. The composite of claim 1, wherein said metal fiber discontinuous phase comprises fibers formed of silicon bronze alloy.

16. The composite of claim 1, wherein said metal fiber discontinuous phase comprises fibers formed of a copper alloy.

17. A vitreous carbon composite including a continuous phase of pyrolyzed poly(furfuryl alcohol) vitreous carbon material polymerized and pyrolyzed about a discontinuous silicon bronze material to form a composite structure including a carbocupric reaction product as a third phase material between the vitreous carbon continous phase and the discontinuous silicon bronze material.

18. The composite of claim 17, wherein the discontinuous silicon bronze is present in the composite in a metal wool form.

19. A metal-reinforced vitreous carbon composite including a metal fiber first discontinuous phase and a thermally non-conductive second discontinuous phase in a continuous phase pyrolyzed poly(furfuryl alcohol) vitreous carbon material.

20. The composite of claim 19, wherein the thermally non-conductive second discontinuous phase comprises particulates of at least one material selected from the group consisting of quartz, silicon, alumina, and silica.

21. A metal-reinforced vitreous carbon composite including a needle-punched metal wool discontinuous phase in a continuous phase pyrolyzed poly(furfuryl alcohol) vitreous carbon material and wherein the composite is essentially free of foam and fume indicia.

22. A pantograph bar comprising a metal-reinforced vitreous carbon composite according to claim 1.

23. A third rail currrent collector comprising a metal-reinforced vitreous carbon composite according to claim 1.

24. A trolley shoe comprising a metal-reinforced vitreous carbon composite according to claim 1.

25. An electrical brush comprising a metal-reinforced vitreous carbon composite according to claim 1.

26. A seal comprising a metal-reinforced vitreous carbon composite according to any claim 1.

27. A therapeutic structure for implantation in an animal body comprising a metal-reinforced vitreous carbon composite according to claim 1.

28. The therapeutic structure of claim 27, comprising a joint replacement structure.

29. A composite according to claim 1, comprising oriented fibers as a discontinuous phase material.

30. A composite according to claim 1, comprising a demetallized porous surface layer.

31. A composite according to claim 1, comprising a textured surface.

32. A multilayer laminate material comprising at least one layer of a vitreous carbon composite including a metal fiber discontinuous phase in a continuous phase pyrolyzed poly (furfuryl alcohol) vitreous carbon.

33. A poly(furfuryl alcohol) film that is essentially free of foam and fume indicia, characterized by a degree of polymerization imparting to the film a flexible character when cast at thicknesses ranging from about 0.1 to about 2,000 $\mu$m.

34. A metal-reinforced poly(furfuryl alcohol) composite green body including a metal fiber discontinuous phase wherein the composite is of a three dimensional character with each of its dimensions being at least 25 millimeters and wherein the composite is essentially free of foam and fume indicia.

35. A composite according to claim 1, comprising a lubricant component therein.

36. A composite according to claim 35, wherein the lubricant component comprises a material selected from the group consisting of molybdenum sulfide, zinc sulfide, metal-free phthalocyanin.

37. A green body precursor of a composite according to claim 1.

38. A process for making a metal-reinforced vitreous carbon composite material that is essentially free of foam and fume indicia, comprising the steps of:

providing a mold including therein a mold cavity and wall structure bounding the mold cavity, wherein the wall structure is formed of a thermally conductive material at a wall thickness providing a substantial thermal heat sink for heat of polymerization of a material polymerized in the mold cavity;

disposing in said mold cavity a metal fiber matrix defining a three-dimensional structure including void space therein;

compressing the three-dimensional structure in the mold to laterally conform the structure to the mold cavity while retaining void space in the three-dimensional structure;

partially polymerizing exterior to the mold cavity a continuous phase precursor material comprising (i) a poly (furfuryl alcohol) monomer and/or oligomer and (ii) a polymerization catalyst, to conduct an exothermic polymerization reaction generating a heat of polymerization;

removing from the partially polymerized precursor material at least part of the heat of polymerization therefrom exterior of the mold cavity;

introducing the partially polymerized precursor material, subsequent to removal of at least part of the heat of polymerization therefrom, into the mold cavity;

compressively consolidating the partially polymerized precursor material with the three-dimensional structure in the mold cavity under polymerization conditions to form a metal-reinforced polymer composite material; and subjecting the metal-reinforced polymer composite material to pyrolysis conditions effective to pyrolize the polymer in the composite material, to yield the metal-reinforced vitreous carbon composite material.

39. The process of claim 38, wherein the precursor material is flowed to the mold cavity along a flow path in which the precursor material is heated to promote said partial polymerization and subsequently is quenched to remove the heat of polymerization from the precursor material.

40. The process of claim 38, wherein the polymerization catalyst comprises a thermally-activated polymerization catalyst.

41. The process of claim 38, wherein the polymerization reaction is quenched by neutralizing the catalyst to provide a predetermined degree of polymerization.

42. The process of claim 38, wherein a moveable wall member is disposed in the mold cavity to subject the three dimensional structure to compression in step (c) and to compressively consolidate the partially polymerized precursor material with the three-dimensional structure in the mold cavity under polymerization conditions in step (g).

43. The process of claim 38, wherein the polymerization conditions in step (g) include heat transfer between the precursor material and the wall structure of the mold.

44. The process of claim 38, further comprising the step of shaping the metal-reinforced polymer composite material prior to subjecting the material to pyrolysis.

45. The process of claim 38, further comprising the step of shaping the metal-reinforced vitreous carbon composite material.

46. The process of claim 38, further comprising the step of lasing a surface of the metal-reinforced vitreous carbon composite material to form a textured surface thereon.

47. The process of claim 38, further comprising the step of etching a surface of the metal-reinforced vitreous carbon composite material to form a textured surface thereon.

48. The process of claim 38, further comprising the step of in-casting a gauze at a surface of the metal-reinforced vitreous carbon composite material to form a textured surface thereon.

49. The process of claim 38, further comprising electrolytically demetallizing the metal-reinforced vitreous carbon composite material at a surface thereof.

50. The process of claim 49, wherein said electrolytically demetallizing step comprises jet impingement of an aqueous electrolytic medium on said surface of the metal-reinforced vitreous carbon composite material.

51. The process of claim 38, further comprising inserting a metal bar into the metal-reinforced polymeric composite material, so that said pyrolysis conditions yield a laminated structural assembly.

52. The process of claim 38, wherein said pyrolysis conditions comprise low frequency induction heating of the metal-reinforced polymeric composite material.

53. The process of claim 38, wherein the polymerization catalyst comprises maleic acid.

54. The process of claim 38, wherein a discontinuous phase material is added to the precursor material in addition to the metal fiber matrix.

55. The process of claim 54, wherein the discontinuous phase material comprises particulates of at least one material selected from the group consisting of quartz, silicon, alumina, and silica.

56. The process of claim 38, comprising incorporating a lubricant component in the composite material.

57. The process of claim 56, wherein the lubricant component comprises a material selected from the group consisting of molybdenum sulfide, zinc sulfide, metal-free phthalocyanin.

58. The process of claim 39, wherein said path is branched into multiple paths in proximity to the mold, whereby quenching of the heat of polymerization is improved over a single path flow of precursor material into the mold.

59. The process of claim 38, wherein said pyrolysis conditions comprise ultrasonic heating of the metal-reinforced polymeric composite material.

60. The process of claim 38, further comprising forming said metal-reinforced vitreous carbon composite material in a selected form, and bonding said composite material to another structural member to form a laminated composite article.

61. The process of claim 60, wherein the laminated composite article comprises a seal assembly.

62. The process of claim 60, wherein the laminated composite article comprises a bearing assembly.

63. The process of claim 60, wherein the laminated composite article comprises a rotary engine rotor tip assembly.

64. The process of claim 60, wherein the laminated composite article comprises an implantable therapeutic structural assembly.

65. The process of claim 60, wherein the laminated composite article comprises a joint prosthesis.

66. The process of claim 60, wherein the laminated composite article comprises a pantograph bar assembly.

67. The process of claim 60, wherein the laminated composite article comprises a third rail current collector assembly.

68. The process of claim 60, wherein the laminated composite article comprises a trolley shoe assembly.

69. The process of claim 60, wherein the laminated composite article comprises an electrical brush assembly.

70. The process of claim 38, wherein the metal fiber matrix comprises a metal wool body.

71. The process of claim 38, wherein the metal fiber matrix comprises an oriented fiber array.

72. A process for forming a metal-reinforced vitreous carbon composite that is essentially free of foam and fume indicia comprising:

providing a metal fiber discontinuous phase;

impregnating the metal fiber discontinuous phase with a precursor including (i) furfuryl alcohol monomer and/or oligomer and (ii) a polymerization catalyst;

polymerizing the precursor;

removing exothermic heat of polymerization from the precursor to maintain temperature of the precursor in a mate range of from about 40° C. to about 100° C., and gel time of the precursor in a range of from about 2 to 30 minutes; and pyrolyzing polymerized precursor to yield the metal-reinforced vitreous carbon composite.

73. A metal-reinforced vitreous carbon composite including a particulate metal discontinuous phase in a continuous phase vitreous carbon that is essentially free of foam and fume indicia, wherein the composite is of a three dimensional character having each of its dimensions being at least 25 millimeters.

74. The composite of claim 73, wherein the particulate metal discontinuous phase comprises a metal selected from the group consisting of copper, copper alloys, nickel, chrome-plated steel, and silicon bronze.

75. The composite of claim 73, wherein the particulate metal discontinuous phase comprises a metal selected from the group consisting of copper and copper alloys.

76. The composite of claim 73, wherein the particulate metal discontinuous phase comprises copper.

77. A metal-reinforced vitreous carbon composite including a metal fiber discontinuous phase in a continuous phase vitreous carbon that is substantially free of void defects, wherein said void defects comprise less than 5% of the composite by volume and the average defect diameter is less than 1 μm, and wherein the composite is of a three dimensional character having each of its dimensions being at least 25 millimeters.

78. The composite of claim 1, wherein said foam and fume indicia form under runaway polymerization conditions.

79. The composite of claim 78, wherein said foam and fume indicia are selected from the group consisting of voids, fissures, and channel artifacts.

80. The composite of claim 1, wherein said foam and fume indicia comprise less than 5% of the composite by volume and the average defect diameter is less than 1 μm.

81. The composite of claim 3, wherein a polymerization thermal management technique is selected from the group consisting of ex situ partial polymerization and discontinuous phase heat transfer to the periphery of the composite mass being formed.

* * * * *

UNITED STATES PATENT AND TRADEMARK OFFICE
CERTIFICATE OF CORRECTION

PATENT NO.    : 6,506,482 B1
DATED         : January 14, 2003
INVENTOR(S)   : Ralph A. Burton and Ralph G. Burton It is certified that error appears in the above-identified patent and that said Letters Patent is hereby corrected as shown below:

<u>Column 7,</u>
Line 14, "instntnent" should be -- instrument --

Signed and Sealed this

Eighth Day of April, 2003

JAMES E. ROGAN
*Director of the United States Patent and Trademark Office*